United States Patent
Trease et al.

(10) Patent No.: US 9,805,910 B1
(45) Date of Patent: Oct. 31, 2017

(54) AUTOMATED SEM NANOPROBE TOOL

(71) Applicant: KLA-Tencor Technologies Corporation, Milpitas, CA (US)

(72) Inventors: David Trease, Alameda, CA (US); Christopher M. Sears, Fremont, CA (US)

(73) Assignee: KLA-TENCOR CORPORATION, Milpitas, CA (US)

( * ) Notice: Subject to any disclaimer, the term of this patent is extended or adjusted under 35 U.S.C. 154(b) by 0 days.

(21) Appl. No.: 14/696,122

(22) Filed: Apr. 24, 2015

Related U.S. Application Data (60) Provisional application No. 62/133,325, filed on Mar. 14, 2015.

(51) Int. Cl.
*H01J 37/28* (2006.01)
*H01J 37/26* (2006.01)
(Continued)

(52) U.S. Cl.
CPC ............ *H01J 37/263* (2013.01); *G01N 23/22* (2013.01); *G01N 23/2204* (2013.01);
(Continued)

(58) Field of Classification Search
CPC ... G01R 31/307; G01R 31/305; H01J 37/261; H01J 37/28; H01J 37/256;
(Continued)

(56) References Cited

U.S. PATENT DOCUMENTS

| 4,733,073 A | 3/1988 | Becker et al. |
| 4,943,769 A * | 7/1990 | Golladay ............ G01R 31/307 324/754.22 |

(Continued)

OTHER PUBLICATIONS

Jagutzki, O., et. al., "Fast Position and time resolved read-out of micro-channel plates with the delay-line technique for single particle and photon detection" Proc. SPIE 3438, Imaging Spectrometry IV, 322 (Oct. 16, 1998).*
(Continued)

*Primary Examiner* — Wyatt Stoffa
(74) *Attorney, Agent, or Firm* — JDI Patent; Joshua D. Isenberg (57) ABSTRACT

Aspects of the present disclosure provide an apparatus comprising a primary beam column configured to direct a primary beam of energetic particles onto a location of interest on a sample containing one or more integrated circuit structures, a detector configured to produce a signal in response to detection of secondary charged particles generated as a result of an interaction between the primary beam of energetic particles and the location of interest, and a signal processor coupled to the detector configured to measure the transient behavior of generation of the secondary charged particles from the signal produced by the detector, and a characterizing module configured to characterize the location of interest by comparing the measured transient behavior to a predetermined reference transient behavior. The detector has a response that is fast enough to detect a transient behavior of generation of the secondary charged particles.

29 Claims, 5 Drawing Sheets

(51) Int. Cl.
*G01N 23/22* (2006.01)
*G01N 23/225* (2006.01)
*H01J 37/256* (2006.01)

(52) U.S. Cl.
CPC ........ *G01N 23/2251* (2013.01); *H01J 37/256* (2013.01); *H01J 37/28* (2013.01)

(58) Field of Classification Search
CPC .... H01J 2237/2806; H01J 2237/24592; G01N 23/22; G01N 23/2204; G01N 23/2251
See application file for complete search history.

(56) References Cited

U.S. PATENT DOCUMENTS

| | | | |
|---|---|---|---|
| 5,057,773 A * | 10/1991 | Golladay | G01R 31/307 324/501 |
| 5,430,305 A | 7/1995 | Cole et al. | |
| 5,982,482 A | 11/1999 | Nelson et al. | |
| 6,737,880 B2 | 5/2004 | Samaan et al. | |
| 6,861,666 B1 | 3/2005 | Weiner et al. | |
| 7,280,945 B1 | 10/2007 | Weiner et al. | |
| 7,786,436 B1 | 8/2010 | Lundquist et al. | |
| 7,952,074 B2 * | 5/2011 | Shinada | G01R 31/305 250/306 |
| 8,536,526 B2 | 9/2013 | Bell et al. | |
| 2003/0071262 A1 * | 4/2003 | Weiner | G01N 21/66 257/48 |
| 2003/0071646 A1 * | 4/2003 | Neo | G01R 31/307 324/754.22 |
| 2003/0179007 A1 * | 9/2003 | Nozoe | G01R 31/307 324/754.22 |
| 2004/0061052 A1 * | 4/2004 | Kim | H01J 37/266 250/307 |
| 2004/0262519 A1 * | 12/2004 | Nam-Koong | G01N 23/2251 250/311 |
| 2005/0006582 A1 * | 1/2005 | Steigerwald | H01J 37/05 250/311 |
| 2005/0139767 A1 * | 6/2005 | Pinto | G01N 21/66 250/307 |
| 2006/0076490 A1 * | 4/2006 | Gunji | G01R 31/305 250/310 |
| 2007/0025610 A1 * | 2/2007 | Adler | G01N 21/956 382/149 |
| 2009/0206428 A1 * | 8/2009 | Meyer | H01L 31/115 257/429 |
| 2010/0072365 A1 * | 3/2010 | Shoham | G01N 23/2208 250/307 |
| 2012/0062269 A1 * | 3/2012 | Patterson | G06T 7/0004 324/762.05 |
| 2012/0153145 A1 * | 6/2012 | Cheng | H01J 37/28 250/307 |
| 2012/0292506 A1 * | 11/2012 | Tsuno | H01J 37/28 250/307 |
| 2012/0318993 A1 * | 12/2012 | Boatner | G01T 1/201 250/368 |
| 2014/0061462 A1 * | 3/2014 | Park | G01N 23/2251 250/307 |
| 2015/0213997 A1 * | 7/2015 | Ward | B82Y 10/00 250/424 |

OTHER PUBLICATIONS

Wurz, Peter, and Lukas Gubler. "Fast microchannel plate detector for particles." Review of scientific instruments 67.5 (1996): 1790-1793.*
Takeshi Nokuo Fault Site Localization Technique by Imaging with Nanoprobes Electronic Device Failure Analysis, vol. 11 http://www.jeolusa.com/DesktopModules/Bring2mind/DMX/Download.aspx?Command=Core_Download&EntryId=601&PortalId=2&TabId=320.
Richard J. Young DualBeam™ Solutions for Electrical Nanoprobing FEI company http://www.surfaceanalysis.ru/technoinfo/products/6b/159/files/1266574320504.pdf.
Wen Pin Lin and Hsiu Ju Chang Physical failure analysis cases by Electron Beam Absorbed Current & Electron Beam Induced Current detection on nano-probing SEM system Quality Division, Powerchip Semiconductor Corp. http://ieeexplore.ieee.org/stamp/stamp.jsp?arnumber=5532245.

* cited by examiner

AUTOMATED SEM NANOPROBE TOOL

CLAIM OF PRIORITY

This application claims the priority benefit of commonly assigned U.S. Provisional Patent Application No. 62/133,325, filed Mar. 14, 2015 the entire disclosures of which are incorporated herein by reference.

FIELD

Aspects of the present disclosure generally relate to imaging and inspection systems, and more particularly to sample inspection by measurement of time dependent response to electronic excitation.

BACKGROUND

Detection of electrical defects on structures formed on a semiconductor wafer is indispensable for improving the productivity of devices. With the development trend in miniature devices, the ability to examine microscopic structures and to detect microscopic defects becomes crucial to the fabrication processes.

Various technologies and methods of defect inspection on structures formed on semiconductor wafers have been developed and employed with varying degrees of success. Optical inspection methods employ optical inspection tools, such as an optical microscope. One example of an optical inspection tool is KLA-Tencor's 29xx Series broadband plasma defect inspection system. This type of device usually involves collecting radiation emitted from a sample or scattered by a sample from an incident beam of radiation directed at the structure. The collected radiation is converted to signals that can be measured or used to form an image. Such measurements or images can be used to determine various characteristics, such as the profile of the structure. The optical inspection tool may also indirectly detect electrical defects caused by some physical or morphological detects either on the wafer surface or below the surface. While optical inspection can be performed fairly fast, it cannot detect subtle electrical defects caused by non-optically visual process issues such as grain boundaries. In addition, optical inspection suffers from a lack of spatial resolution, making it difficult to precisely identify defective features on the wafer.

Another method uses scanning electron microscopes (SEMs) for detection of electrical defects. Secondary charged particles are emitted from a surface of the specimen to be examined when electron or ion source impinges on the surface with sufficient energy. Since the energy and/or the energy distribution of such secondary charged particles offers information as to the topography of the specimen, SEMs are employed to detect the secondary charged particles and convert them to electrical signals used to generate images of the specimen for defect inspection. SEM inspection allows location of electrical defects with submicron position accuracy. KLA-Tencor eS8xx Series tools and Hermes Microvision eScanxxx Series tools are the examples of SEM tools that are widely used. However, SEM tools are insensitive to certain types of electrical defects.

Next, physical electrical probing of defects has been a standard part of quality control for integrated circuits. Existing "nanoprobing" tools allows spatial resolution of 5 nm. However, nano-scale physical probing is usually slow. Automation is difficult and the process can be highly labor-intensive. Thus, it is desirable to develop a fast inspection tool that is sensitive to transient and subtle voltage contrast defects.

It is within this context that aspects of the present disclosure arise.

BRIEF DESCRIPTION OF THE DRAWINGS

Objects and advantages of aspects of the present disclosure will become apparent upon reading the following detailed description and upon reference to the accompanying drawings in which:

FIG. 2a flow diagram illustrating analysis of time dependent response to electronic excitation of surface features according to an aspect of the present disclosure.

SUMMARY

According to aspects of the present disclosure, an apparatus comprises a primary beam column configured to direct a primary beam of energetic particles onto a location of interest on a sample containing one or more integrated circuit structures, a detector configured to produce a signal in response to detection of secondary charged particles generated as a result of an interaction between the primary beam of energetic particles and the location of interest, and a signal processor coupled to the detector configured to measure the transient behavior of generation of the secondary charged particles from the signal produced by the detector, and a characterizing module configured to characterize the location of interest by comparing the measured transient behavior to a predetermined reference transient behavior. The detector has a response that is fast enough to detect a transient behavior of generation of the secondary charged particles In some implementations, the primary beam of energetic particles is a beam of electrons and wherein the secondary charged particles are secondary electrons.

In some implementations, the detector has a time resolution of about 10 ns better.

In some implementations, the primary beam column is configured focus the beam to a beam spot at the location of interest and to direct the primary beam to the location of interest with sufficient accuracy that that more than about 80%, of a beam spot of the primary beam lands on location of interest.

Another aspect of the present disclosure provides a method comprising directing a primary beam of charged particles onto a location of interest on a sample containing one or more integrated circuit structures, detecting secondary charged particles generated as a result of an interaction between the beam of charged particles and the location of interest, measuring a transient behavior of generation of the secondary charged particles and characterizing the location by comparing the measured transient behavior to a predetermined reference transient behavior.

DETAILED DESCRIPTION

Although the following detailed description contains many specific details for the purposes of illustration, anyone of ordinary skill in the art will appreciate that many variations and alterations to the following details are within the scope of the present disclosure. Accordingly, the exemplary embodiments of the invention described below are set forth without any loss of generality to, and without imposing limitations upon, the claimed invention.

INTRODUCTION

U.S. Pat. Nos. 4,943,769 and 5,057,773 describe a way of testing electrical connections and short circuits of conductor networks on a body of insulating material without physical contact. Contacts are probed with an electron beam in conjunction with charging a larger surface area with a flood beam. First and second probe measurements are taken at one contact before and after discharging a second contact. A differences between the first and second probe measurements indicates whether there is a conductive path between the two contacts. Although this information may be useful, it turns out there is additional information that may be gathered by looking at the time evolution of a transient to surface excitation. This information may be completely missed if only two probe measurements are taken.

Aspects of the present disclosure arise from recognizing that in a SEM-type inspection system transient and subtle electrical defects can be masked by larger-scale bulk greylevel variation between the sample and the reference.

Aspects of the present disclosure provide an SEM inspection tool in association with nanoprobing techniques. Nanoprobing techniques can be used with SEMs to achieve higher spatial resolution. This allows fault site localization down to an individual transistor level.

In addition, aspects of the present disclosure provide an SEM tool with the ability to detect previously undetectable defects in an integrated circuit by assessing the time-dependent response to surface electronic excitation by an electron beam. By way of example and not by way of limitation, an SEM inspection tool in association with nanoprobing techniques according to the present disclosure may detect grain dislocation defects that cause conductivity of the contact to behave differently.

Figure 1A:
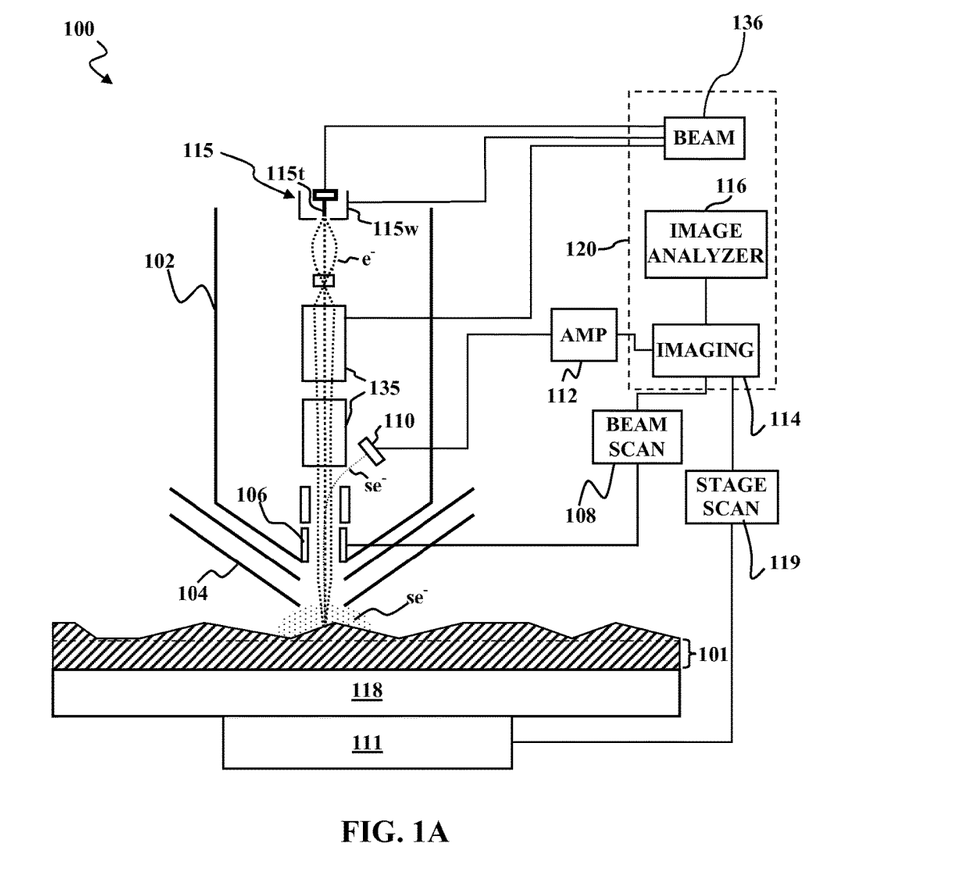
FIG. 1A is a schematic diagram of a charged particle beam system adapted to implement analysis of time dependent response to electronic excitation of surface features according to an aspect of the present disclosure.
Figure 1B:
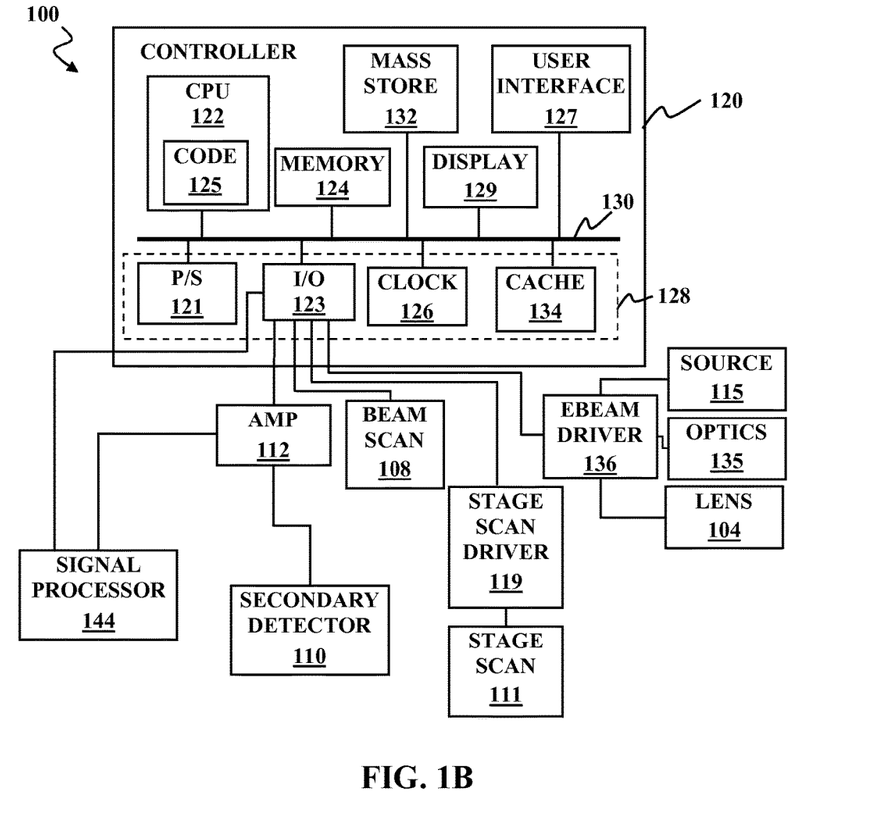
FIG. 1B is a block diagram of the system of FIG. 1A.

FIG. 1A and FIG. 1B illustrate an example of a charged particle beam system 100 that incorporates certain aspects of the present disclosure. In this non-limiting example, the system 100 is configured as a scanning electron microscope (SEM) having charged particle optical column 102 with an electron source 115, beam optics elements 135, an immersion lens 104. The optical column 102 may be controlled by electronics 136, referred to herein as a beam driver. The beam driver 136 may control the electron source 115, beam optics elements 135 and immersion lens 104. In this example, the beam optics 135 include two or more electrically conductive cylinders maintained at voltages that produce electric fields to extract electrons from the source 115 and form them into a primary beam 103 that travels in the direction of a sample 101. The immersion lens 104 focuses the primary beam into a narrow spot at the surface of the sample.

By way of example and not by way of limitation, the electron source 115 may be a field emission source. A field emission device comprises a field emitter cathode and an anode spaced from the cathode. The cathode may be a tip or needle field emitter element 115$t$ and the anode may be a Wehnelt cylinder 115$w$ that acts as a convergent electrostatic lens. A bias voltage applied to the Wehnelt cylinder 115$w$ creates a repulsive electrostatic field that condenses the cloud of primary electrons produced by the cathode of the electron source 115. Although a single field emitter element 115$t$ is shown in FIG. 1A, those skilled in the art will recognize that the electron source 115 may include a field emitter array containing multiple field emission devices, which may be independently controllable.

The beam optics elements 135, an immersion lens 104 focus a beam of electrons $e^-$ from the electron source 115 onto a surface of the sample 101, which may be an integrated circuit wafer or a test wafer. The sample 101 is supported by a stage 118. The electrons may be scanned across the surface of the sample 101 by one or more beam deflectors 106, which may be implemented, e.g., as one or more electrostatic deflector plates. In such an implementation, voltages provided to the deflector plates 106 via a beam scanner driver 108 provide electric fields that deflect the primary beam $e^-$. In alternative implementations, the beam deflectors 106 may be implemented as one or more magnetic coils. In such implementations the beam scanner driver 108 may apply currents to such coils to scan the primary beam $e^-$ across the sample 101. Alternatively, the stage 118 may include a stage scanning mechanism 111 and stage scanner driver 119 configured to move the sample along an X-Y plane parallel to the surface of the sample 101 in one or more directions relative to the optical column 102. In some implementations the stage scanning mechanism 111 and stage scanner driver 119 may move the stage in one direction (e.g., the X direction) as the beam scanner driver 108 scans the beam in a different direction (e.g., the Y direction) in a line scan.

By way of example, and not by way of limitation, images may be generated by driving the beam scanner in a raster pattern in which the primary beam scans across the sample 101 in one direction with the beam scanner driver 108 and beam scanner coils 106 (or deflector plates) and the detector signal as a function of beam position is converted into a line of the image as is well known in the art. At an end of the scan of the beam in one direction (e.g., the X-direction), the beam location may be adjusted by a small amount (e.g., an amount comparable to a size of the beam spot on the sample) in a different direction (e.g., the Y-direction) and another scan may be performed to generate another line of the image. By repeating this process an image of part of the sample may be generated.

In alternative implementations, images may be generated by scanning the beam of electrons $e^-$ across the sample 101 in a line scan one direction (e.g., the X-direction) and converting the secondary detector signal as a function of beam position into a line of the image. The stage scanner driver 119 and stage scanning mechanism may translate the sample 101 by a small amount in a different direction (e.g., the Y-direction) at the end of each line scan.

Alternatively, the stage scanner driver 119 may drive the stage in both the X and Y directions relative to the optical column 102 to scan the beam across the sample while the beam remains fixed relative to the optical column.

Electrons $e^-$ striking the sample 101 are either backscattered or initiate secondary emission. The electron beam column collects a portion of such backscattered or secondary electrons $se^-$ (or other secondary particles, such as ions, X-rays, or ultraviolet photons) that emerge from the surface of the sample 101. In the illustrated example of the system 100, secondary particle detector is located off-axis and a deflector, e.g., a Wien filter deflects secondary particles se⁻ that are collected by the optical column 102, toward the detector 110. A Wien filter provides an ExB field, i.e., one in which electric and magnetic fields are perpendicular to each other and to the primary beam's path. The electric and magnetic fields exert oppositely directed forces on the primary beam. The magnitude of the magnetic force depends on strength of the magnetic field and the speed of the particles in the primary beam but the magnitude of the electric force depends only on the strength of the electric field. The Wien filter is normally calibrated to allow primary beam to pass straight through, while secondary electrons, which travel in the opposite direction are deflected by the Wein to the detector 110.

The secondary particle detector 110 is configured to detector backscattered primary electrons or secondary electrons se⁻ that travel back up into the electron beam column 102 and impinge on a secondary particle detector 110, which generates a secondary signal that is proportional to the amount of backscattering or secondary emission. The signal may be amplified by an amplifier 112. In an imaging mode, the amplified signal and a signal from the beam scanner driver 108 and/or stage scanner driver 119 are combined by an image generator 114 to produce a magnified image of the surface of the sample 101. Images generated by the image generator 114 may be analyzed by the image analyzer 116, e.g., to determine a measure of quality of the modified surface or shape and size of resulting formed structures.

The secondary particle detector 110 is generally configured to generate a signal in response to secondary particles se⁻ arriving at the detector. The design of the secondary particle detector 110 may depend on the type of particles being detected. In certain implementations, the secondary particle detector 110 may be a scintillator and the amplifier 112 may be a photomultiplier tube. A scintillator includes a luminescent material that emits photons when struck by sufficiently energetic particles. A photomultiplier tube amplifies a signal of incoming photons though generation of electrons at a photocathode via the photoelectric effect and multiplication of electrons at a series of dynodes via secondary electron emission. In alternative implementations, the detector 110 may be a diode device with a junction and depletion region. Examples of such devices include, but are not limited to PN junction detectors, or PIN junction diode detectors, CMOS detectors (e.g., a charge coupled device (CCD)), silicon-based or III-V detectors, multi-channel plates, photodiode arrays, avalanche photodiodes and/or Schottky diode.

As shown in the block diagram of FIG. 1B, the image generator 114 and image analyzer may be part of a controller 120. The controller 120 may be a self-contained microcontroller. Alternatively, the controller 120 may be a general purpose computer configured to include a central processor unit (CPU) 122, memory 124 (e.g., RAM, DRAM, ROM, and the like) and well-known support circuits 128 such as power supplies 121, input/output (I/O) functions 123, clock 126, cache 134, and the like, coupled to a control system bus 130. The memory 124 may contain instructions that the CPU 122 executes to facilitate the performance of the system 100. The instructions in the memory 124 may be in the form of the program code 125. The code 125 may control, e.g., the electron beam voltage and current produced by the source 115, the focusing of the beam with the beam optics 135 and the immersion lens 104, the scanning of the electron beam by the coils 106, the scanning of the stage 118 by the stage scanner 111 and the formation of images with the signal from the secondary particle detector 110 in a conventional fashion. The code 125 may also implement analysis of the images.

The code 125 may conform to any one of a number of different programming languages such as Assembly, C++, JAVA or a number of other languages. The controller 120 may also include an optional mass storage device, 132, e.g., CD-ROM hard disk and/or removable storage, flash memory, and the like, which may be coupled to the control system bus 130. The controller 120 may optionally include a user interface 127, such as a keyboard, mouse, or light pen, coupled to the CPU 122 to provide for the receipt of inputs from an operator (not shown). The controller 120 may also optionally include a display unit 129 to provide information to the operator in the form of graphical displays and/or alphanumeric characters under control of the processor unit 122. The display unit 129 may be, e.g., a cathode ray tube (CRT) or flat screen monitor.

The controller 120 may exchange signals with the imaging device scanner driver 108, the e-beam driver 135 and the detector 110 or amplifier 112 through the I/O functions 123 in response to data and program code instructions stored and retrieved by the memory 124. In some implementations, a signal processor 144 may perform preliminary signal conditioning on amplified signals from the amplifier 112 and send the conditioned signals to the controller, e.g., via the I/O functions 123. Depending on the configuration or selection of controller 120, the scanner driver 108, detector 110, and/or amplifier 112 may interface with the I/O functions 123 via conditioning circuits. The conditioning circuits may be implemented in hardware or software form, e.g., within code 125. Also, in some implementations, the functions of the signal processor 144 may be implemented in software within the code 125.

Figure 2:
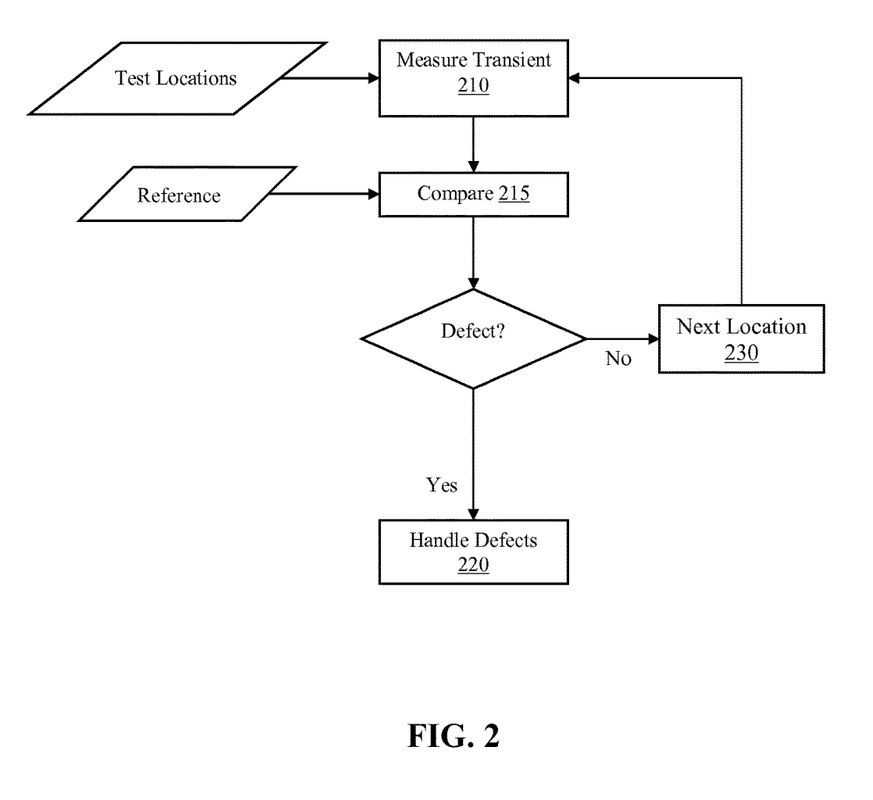

In accordance with aspects of the present disclosure, the code 125 may be configured to analyze time dependent response to electronic excitation of surface features of the sample 101. The flow diagram FIG. 2 illustrates an example of a method for analysis of time dependent response to electronic excitation of surface features that may be implemented by execution of portions of the code 125.

To implement transient response detection in accordance with aspects of the present disclosure, it is desirable for certain components of the system 100 to have particular characteristics. In general it is desirable for the detector 110 to have a response that is sufficiently fast to detector to detect transient phenomena on a time scale of interest. The time scale of interest is dependent on the time dependent nature of the transient phenomena. Specifically, in some implementations, but not all, it may be particularly useful for the secondary detector 110 to have response that is fast enough to measure the transient response with a time resolution of about 10 ns or better, preferably about 2 ns or better to be able to detect certain types of defects. Examples of suitable types of detectors include multi-channel plate (MCP), solid state particle detectors and certain fast scintillators that combine a scintillator and photomultiplier tube. It is noted that slower detectors may be useful for detector transient phenomena that take place over longer time scales.

Not all SEM systems have the ability to filter out the backscattered electrons. A typical SEM system detects the energetic backscattered electrons to generate an image and has a high pass filter to filter out the lower energy secondary electrons. Aspects of the present disclosure, by contrast rely upon detection of the secondary electrons. The system 100 may include a low pass filter to back out the backscattered electrons. Alternatively, if the backscattered electron signal is known well enough the signal processor 114 could subtract it out.

According to aspects of the present disclosure, the system 100 can be configured to implement a method of defect characterization through measurement of transient secondary response of the features of interest. The flow diagram of FIG. 2 illustrates such a method. In step 210, the primary beam e⁻ is directed to an inspection site and the beam is centered on a feature of interest (e.g., gate, contact, etc.) that is to be inspected, e.g., by applying appropriate voltages to the deflector plates 106. Alternatively, the stage scanner driver 119 may direct the stage scanning mechanism 111 to move the stage 118 so that the beam e⁻ lands on the feature of interest. Furthermore, the beam may be directed to the feature of interest by a combination of stage movement and beam deflection. The inspection site is exposed to the primary beam for a given time, t, while secondary electrons se⁻ emitted from the sample surface as a result of an interaction between the primary beam and the inspection site are collected and detected by the SEM tool's electron detector 110 as a function of time.

According to aspects of the present disclosure, at least three measurements are made at different times during the course of a given transient event. The transient event may last for between about 1 nanosecond and about 1 microsecond. Taking at least three measurements can reveal information that would otherwise be obscured if only two measurements were taken. It is noted that the transient behavior that is being measured may be triggered, e.g., by the primary beam 103, before the first measurement is taken and may end after the last measurement is taken. It is therefore useful to distinguish between the "transient interval", which is the time over which the transient event occurs, and the "measurement interval" which is essentially the time between the beginning of the first measurement and the end of the last measurement for a given transient interval. The time between successive measurements during the measurement interval is referred to herein as the sample interval, which may be fixed or variable. The sample interval is generally limited by the response speed of the detector 110.

By way of example, and not by way of limitation, the transient interval may last from about 1 nanosecond to about 1 microsecond. By way of example, and not by way of limitation, the measurement interval may last from about 1 nanosecond to about 200 nanoseconds, more particularly, from about 10 nanoseconds to about 100 nanoseconds.

More than three measurements may be taken during the measurement interval if the response of the detector 110 is sufficiently fast. By way of example, and not by way of limitation, for a fixed sample interval, an upper limit on the number of measurements that can be taken in the measurement interval may be approximated by the measurement interval divided by the sample interval. By way of example, and not by way of limitation, the number of measurements taken during the measurement interval, including the first and last measurements, may be 3, 4, 5, 6, 7, 8, 9, 10, any number between 3 and 100, or any number between 3 and 1000. Even more measurements could be taken if the detector response is fast enough. Generally speaking, taking more measurements during the measurement interval increases the amount of detail that can be observed in the transient behavior.

In some implementations, additional processing may be performed on the raw signal from the detector 110 to map the raw signal to a physical property of the sample 101. By way of example, one possible property of interest is the secondary electron yield of the sample 101. The yield of secondary electrons from the sample is a function of the surface potential. The surface potential that is developed during electron irradiation is a function of the capacitance of the sample. The signal at the detector, therefore, may be mapped to the sample capacitance, if the mappings of detector signal to secondary electron yield, secondary electron yield to surface potential and surface potential to sample capacitance are sufficiently well understood A curve of detector signal versus time can be thus acquired and such a curve illustrates a transient behavior of time dependent response to electronic excitation of surface features at the inspection site. In step 215, the acquired curve is compared with a reference curve of a non-defective reference area. When there is a significant difference between the measured curve and a reference curve, a defect candidate is identified and it will be handled by conventional methods in step 220. Otherwise, no defect is detected. The electron beam is then directed to a next site in step 230. The above steps are repeated. As such, voltage contrast defects may be detected by comparison of the acquired curve of time dependent response to electronic excitation of surface features with a reference curve.

In some implementations, the system 100 uses a 250 nA probe beam. A lower beam current is used in order to see the transient behavior that includes effects of circuitry connected to the inspection site. In some implements, the system has a 64 micron field of view at 2048×2048 pixels. In other implements, the system has a 0.5 micron field of view at 512×512 pixels. In some implementation, the primary beam column focuses the beam spot to a spot size of about 100 nanometers or less. It is desirable for the beam placement to be sufficiently accurate that all or nearly all (e.g., better than 80%, probably 90% or better) of the beam spot lands on the feature to be analyzed. Such accuracy may be accomplished by suitable configuration of the beam deflectors 106, beam scanner driver 108, the stage 111, the stage scanner 118, the stage scanner driver 119 or some combination of two or more of these.

Conventional techniques may be used to identify locations of interest on the sample 101 for probing. Aspects of the present disclosure can "piggy-back" on software and hardware architecture available for existing SEM review tools to define features for probing. By way of example and not by way of limitation, placement of the primary beam may be facilitated by aligning the coordinate system of the tool to a design clip from the sample.

Figure 3:
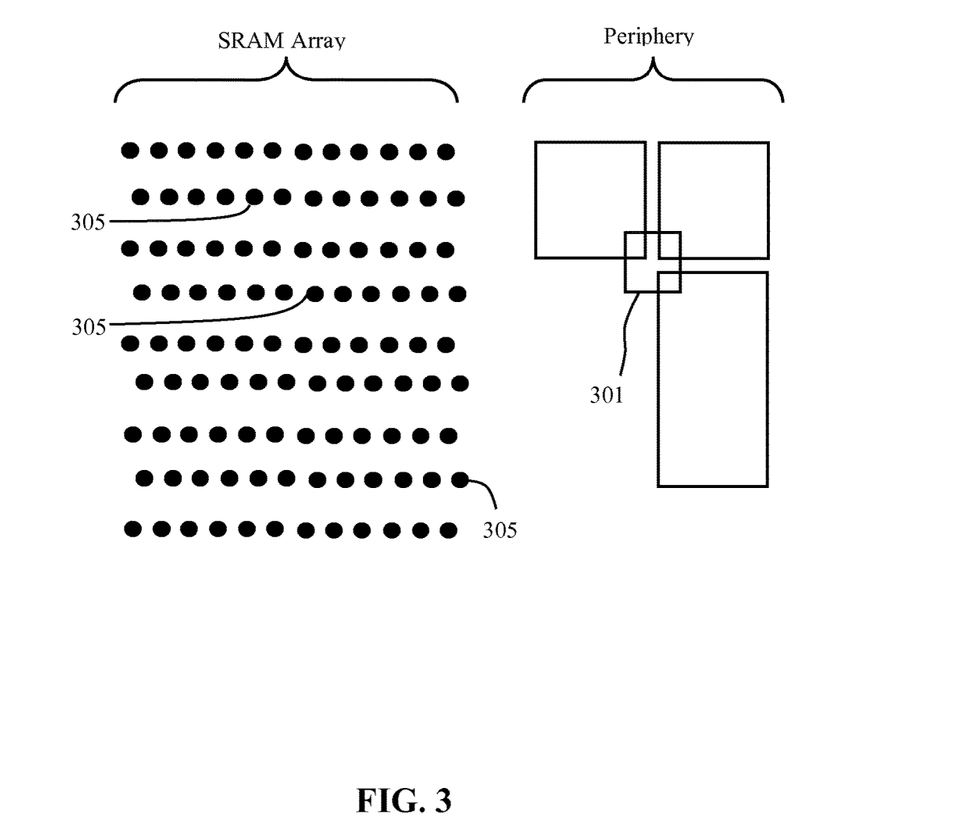
FIG. 3 is a schematic plan view of a portion of an integrated circuit illustrating an example of the use of alignment marks to locate features that are to be analyzed for defects using electronic excitation of surface features according to an aspect of the present disclosure.

FIG. 3 schematically illustrates an example of the use of alignment marks to locate features 305 that are to be analyzed for defects using electronic excitation of surface features. By way of example, and not by way of limitation, these targets 305 may include tungsten electrical contacts or polysilicon gates. The locations of these features 305 may be defined in relation to a unique anchor site 301.

By way of example, and not by way of limitation, a user may select the features 305 to probe by generating a results file based on a design clip, as discussed above. A particular contact 305 that is to be inspected may be located by first locating a known reference point 301 and determining a vector from the reference point 301 using the design clip for the device. As used herein, and as generally understood by those skilled in the art, the term "design clip" refers to a set of computer graphic images of a device and corresponding computer data that details where all the devices features are relative to each other in the device design. It is common for a device design to include reference features sometimes called "anchor sites" that are typically placed in inactive regions of the device layout that are used as fiducial marks (e.g., the peripheral region of the device). It is noted that SEM images of these locations are not acquired. It is sufficient to know the vector between anchor site and the inspection site.

In alternative implementations, the user may specify features to inspect by manually selecting them with a user interface (UI) for the system 100 rather than specifying the site locations from a design clip.

In an automated mode of operation, the SEM tool 100 may be driven to an anchor site that is close to a feature of interest. An image may then be obtained of a field of view that includes the anchor site and surrounding portions of the device. A pattern matching algorithm may then be applied to the image to align the SEM field of view to the anchor site. Alignment of SEM field of view with an anchor site may allow high spatial location accuracy. Upon alignment of SEM field of view with anchor site, the electron beam may be directed to the feature of interest that is to be inspected.

Figure 4A:
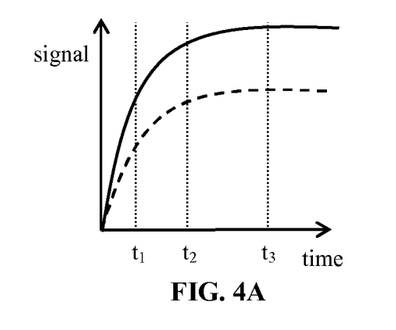
FIGS. 4A-4D are graphs illustrating time dependent response to electronic excitation of surface features according to an aspect of the present disclosure.
Figure 4B:
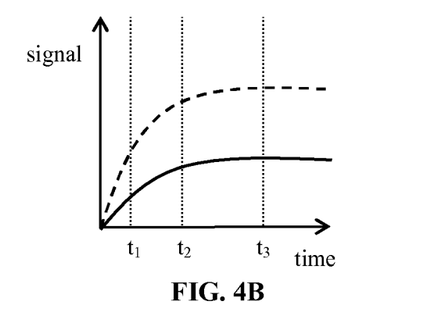

FIGS. 4A-4D illustrates hypothetical examples of plots of detector signal versus time. It is assumed for the purposes of these examples that the detector signal is proportional to secondary electron yield. Using this technique, secondary electron yield versus time curves for all inspection sites may be generated for each die on a semiconductor wafer. The system 100 may then compare each such curve to a reference curve. Potentially defective sites may be identified when the yield curve differs significantly from a nominal "good" reference curve. By way of example, and not by way of limitation, the comparison may look for differences in the time dependence of the yield curve by comparing measurements taken at three times $t_1$, $t_2$ and $t_3$, as indicated by the vertical dashed lines to corresponding reference values at these times. In FIG. 4A, the measured curve for a defective contact (indicated by solid lines) is above the reference curve (indicated by the dashed line). The defect represented by the measured yield curve in FIG. 4A would be visible as bright voltage contrast in conventional eBeam inspection. In FIG. 4B, the measured curve is below the reference curve. The defect represented by the measured yield curve in FIG. 4B would be visible as dark voltage contrast in conventional eBeam inspection.

Figure 4C:
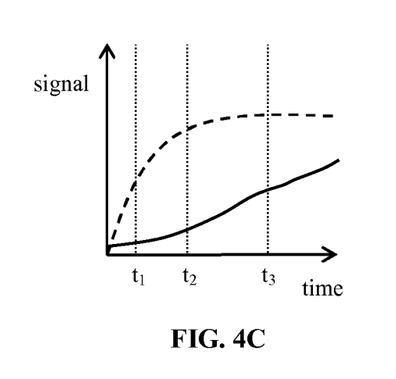
Figure 4D:
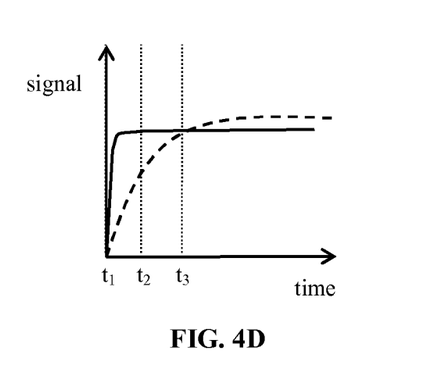

Although defects that would produce the measured yield curves are detectable by conventional electron beam inspection systems not all defects are so detectable. Specifically, transient voltage contrast is very difficult or impossible to detect with a conventional electron beam inspection or review tool. FIG. 4C and FIG. 4D depict examples of electron yield curves for defective contacts (solid line) in comparison to nominal "good" candidate (dotted line). These curves represent examples of "transient" voltage contrast, which is very difficult or impossible to detect using conventional eBeam inspection tools but which is readily observable with systems configured in accordance with aspects of the present disclosure. In particular, note that in a case, such as FIG. 4D where the initial measurements taken at $t_1$ and the final measurements taken at $t_3$ are the same for both the "good" and "defective" transients but the intermediate measurements at $t_3$ is very different. A system that captured only the initial and final measurements would miss this subtle difference in transient behavior.

Aspects of present disclosure allow rapid detection of defects which are currently undetectable with any existing automated defect detection methodology (e.g., dislocations, grain boundaries). Specifically, users may select probe inspection sites using design clips and probe the sites with nanometer-scale accuracy. Thus, unlike existing eBeam inspection techniques, the system according to the present disclosure is sensitive to transient and subtle voltage contrast defects (e.g., in a Tungsten chemical mechanical polish (WCMP) layer) and is capable of identifying very small capacitance differences on structures of interest. The system according to the present disclosure may also enable identification of killer gap defects.

In addition, the system according to the present disclosure allows fast SEM voltage contrast inspection. Other than acquiring initial "anchor" image, the electron beam only needs to visit target sites for probing. By removing the need for imaging large areas of the wafer, the throughput of the voltage contrast inspection can be dramatically increased. The time to probe a single feature is simply equal to the amount of time to acquire the yield profile plus the time to deflect the beam to the site.

Furthermore, aspects of present disclosure may be integrated with existing SEM review tools (e.g., existing CPI Align-by-Design framework on KLA-Tencor eDR-7xxx review tool).

According to aspects of this disclosure, there are a number of different ways in which the transient behavior of generation of the secondary charged particles from the signal produced by the detector may be measured. In some implementations it is possible to extract the transient behavior from information contained in conventionally acquired SEM images. For example, if the beam scanning mechanism 106 and beam scanner driver 108 can scan primary beam can be scanned sufficiently fast and the detector 110 is sufficiently sensitive the image generator 114 could generate images the sample 101 quickly compared to the time scale of the transient behavior. In such a case, the image analyzer 116 could measure the transient behavior by comparing the secondary signal at a fixed sample location for an initial frame and two or more subsequent frames.

Alternatively, it is possible in principle to acquire the transient behavior information from a conventionally acquired SEM image through signal processing. Specifically, as the primary beam e⁻ scans across the sample 101 during imaging different parts of the image exhibit different secondary yield over time. This may be envisaged as a variation in brightness for adjacent pixels in a line along the scan path of the primary beam. Although the transient behavior information is arguably present in the data for every SEM image, the transient behavior is not "measured" until signal processing is performed on the image to deconvolve the transient behavior from the pixel data. The pixel data for an SEM image may be regarded as representing a convolution of the transient secondary electron yield behavior with other behaviors characteristic of the interaction between the primary beam and the location of interest on the sample over time as the primary beam sweeps across the sample. If these behaviors are sufficiently well understood the transient behavior may be measured by deconvolution of the pixel data.

It is noted that aspects of the present disclosure are not limited to the described examples. For example, although a primary beam of electrons is described, the primary beam may be a beam of other charged energetic particles (e.g., ions) or neutral energetic particles, e.g., neutrons or energetic photons (e.g., ultraviolet, X-ray, gamma ray, and the like).

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. In the claims that follow, the indefinite article "A", or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. An apparatus, comprising:
a primary beam column configured to direct a primary beam of energetic particles onto a location of interest on a sample containing one or more integrated circuit structures, wherein the primary beam column is configured to direct the primary beam to a next location of interest after each transient emission of secondary charged particles that is triggered by irradiation of the location of interest by the primary beam;
a detector configured to produce a signal in response to detection of secondary charged particles generated as a result of an interaction between the primary beam of energetic particles and the location of interest, wherein the detector has a response that is fast enough to obtain three or more measurements within about 10 ns or less during a measurement interval; and
a signal processor coupled to the detector configured to measure behavior of generation of the secondary charged particles from the signal produced by the detector; and
a characterizing module configured to characterize the location of interest by comparing the three or more measurements to a predetermined reference behavior of secondary charged particles versus time for a non-defective reference area.

2. The apparatus of claim 1, wherein the primary beam of energetic particles is a beam of electrons.

3. The apparatus of claim 1, wherein the secondary charged particles are secondary electrons.

4. The apparatus of claim 1, wherein the primary beam of energetic particles is a beam of electrons and wherein the secondary charged particles are secondary electrons.

5. The apparatus of claim 1, wherein the detector has a time resolution of about 2 ns or better.

6. The apparatus of claim 1, further comprising a filter configured to reduce or remove a component of a signal corresponding to backscattered energetic particles from the primary beam.

7. The apparatus of claim 1, wherein the primary beam column includes one or more deflectors configured to direct the primary beam to different locations on the sample.

8. The apparatus of claim 7, wherein the primary beam column is configured to focus the beam to a beam spot at the location of interest and to direct the primary beam to the location of interest with sufficient accuracy that that more than about 80%, of a beam spot of the primary beam lands on location of interest.

9. The apparatus of claim 7, wherein the primary beam column is configured to focus the primary beam to a spot size of about 100 nanometers or less.

10. The apparatus of claim 1, further comprising a sample stage configured to retain the sample and a scanning mechanism configured to translate the sample in one or more directions.

11. The apparatus of claim 1, wherein the signal processor is configured to generate three or more successive images of a region of the sample from a signal from the detector containing the location of interest and measure a transient behavior by comparing the signal value at the location of interest for the three or more successive images.

12. The apparatus of claim 1, wherein the a signal processor is configured to generate an image of a region of the sample from a signal from the detector containing the location of interest and measure a transient behavior by analyzing the signal for adjacent pixels within the image at location of interest.

13. The apparatus of claim 1, wherein the three or more measurements include 3, 4, 5, 6, 7, 8, 9, or 10 measurements.

14. The apparatus of claim 1, wherein the three or more measurements include between 3 and 100 measurements.

15. The apparatus of claim 1, wherein the three or more measurements include between 3 and 1000 measurements.

16. The apparatus of claim 1, wherein the measurement interval is between about 1 nanosecond and about 200 nanoseconds in duration.

17. The apparatus of claim 1, wherein the measurement interval is between about 10 nanosecond and about 100 nanoseconds in duration.

18. A method, comprising:
directing a primary beam of energetic particles from a primary beam column onto a location of interest on a sample containing one or more integrated circuit structures, wherein the primary beam is directed to a next location of interest after each transient emission of secondary charged particles that is triggered by irradiation of the location of interest by the primary beam;
detecting secondary charged particles generated as a result of an interaction between the primary beam of energetic particles and the location of interest with a detector;
measuring a behavior of generation of the secondary charged particles, wherein three or more measurements are obtained within about 10 ns or less over the course of a measurement interval; and
characterizing the location by comparing the three or more measurements to a predetermined reference behavior of secondary charged particles versus time for a non-defective reference area.

19. The method of claim 18, wherein the primary beam of energetic particles is a beam of electrons.

20. The method of claim 18, wherein the secondary charged particles are secondary electrons.

21. The method of claim 18, further comprising directing the primary beam of energetic particles onto a next location of interest on the sample.

22. The method of claim 18, wherein measuring a transient behavior includes generating two or more successive images of a region of the sample from a signal from the detector containing the location of interest and comparing the signal value at the location of interest for the two or more successive images.

23. The method of claim 18, wherein measuring a transient behavior includes generating an image of a region of the sample from a signal from the detector containing the location of interest and analyzing the signal for adjacent pixels within the image at location of interest.

24. The method of claim 18, wherein the three or more measurements include 3, 4, 5, 6, 7, 8, 9, or 10 measurements.

25. The method of claim 18, wherein the three or more measurements include between 3 and 100 measurements.

26. The method of claim 18, wherein the three or more measurements include between 3 and 1000 measurements.

27. The method of claim 18, wherein the measurement interval between about 1 nanosecond and about 200 nanoseconds in duration.

28. The method of claim 18, wherein the measurement interval between about 10 nanosecond and about 100 nanoseconds in duration.

29. A non-transitory computer-readable medium having computer executable instructions embodied therein, the computer executable instructions being configured to implement a method when executed, the method comprising:

directing a primary beam of energetic particles from a primary beam column onto a location of interest on a sample containing one or more integrated circuit structures, wherein the primary beam is directed to a next location of interest after each transient emission of secondary charged particles that is triggered by irradiation of the location of interest by the primary beam;

detecting secondary charged particles generated as a result of an interaction between the primary beam of energetic particles and the location of interest with a detector;

measuring a behavior of generation of the secondary charged particles, wherein three or more measurements are obtained within about 10 ns or less over the course of a measurement interval; and characterizing the location by comparing the three or more measurements to a predetermined reference behavior of secondary charged particles versus time for a non-defective reference area.

* * * * *